United States Patent [19]
Fischer et al.

[11] Patent Number: 6,022,988
[45] Date of Patent: Feb. 8, 2000

[54] PREPARATION OF 3-CYANO-3, 5, 5-TRIMETHYLCYCLOHEXANONE

[75] Inventors: Jakob Fischer, Kirchdorf; Wolfgang Siegel, Limburgerhof; Volker Bomm, Mutterstadt; Martin Fischer, Ludwigshafen; Klaus Mundinger, Limburgerhof, all of Germany

[73] Assignee: BASF Aktiengesellschaft, Ludwigshafen, Germany

[21] Appl. No.: 09/372,062

[22] Filed: Aug. 11, 1999

[30] Foreign Application Priority Data

Aug. 12, 1998 [DE] Germany .............. 198 36 474

[51] Int. Cl.[7] ................................. C07C 253/10
[52] U.S. Cl. ........................................... 558/341
[58] Field of Search ................................. 558/341

[56] References Cited

U.S. PATENT DOCUMENTS

| | | | |
|---|---|---|---|
| 4,299,775 | 11/1981 | Dubreux | 558/341 |
| 5,011,968 | 4/1991 | Thunberg et al. | 558/341 |
| 5,179,221 | 1/1993 | Takahoso et al. | 558/341 |
| 5,183,915 | 2/1993 | Forguy et al. | 558/341 |
| 5,516,928 | 5/1996 | Mundinger et al. | 558/341 |

FOREIGN PATENT DOCUMENTS 291 074 11/1988 European Pat. Off. .
502 707 9/1992 European Pat. Off. .

OTHER PUBLICATIONS

Jahn et al., Tetrahedron Lett. 38, 3883–4 (1997).
Weinheimer et al., Tetrahedron 29, (1973) 3135–6.
Chem. Abst 105:42383u; JP 61 033 157, 1986.
OZ 44679 = U.S. 5,516,928, Mar. 4, 1994.
OZ 49267 = German 198 364 77.6, Aug. 11, 1998.

*Primary Examiner*—Fiona T. Powers
*Attorney, Agent, or Firm*—Keil & Weinkauf

[57] ABSTRACT

In a process for preparing 3-cyano-3,5,5-trimethylcyclohexanone by reacting isophorone with hydrogen cyanide at from 80 to 220° C. in the presence of a catalyst, the reaction is carried out in the presence of the betaine 1,3-dimethylimidazolium-4-carboxylate.

5 Claims, No Drawings

PREPARATION OF 3-CYANO-3, 5, 5-TRIMETHYLCYCLOHEXANONE

The present invention relates to a process for preparing 3-cyano-3,5,5-trimethylcyclohexanone(isophorone nitrile, IPN) by reacting isophorone (IP) with hydrogen cyanide (HCN) at from 80 to 220° C. in the presence of a catalyst.

Isophorone nitrile (IPN) is an intermediate for preparing isophoronediamine (IPDA) which is used as an epoxy hardener or as monomer for polyamines and polyurethanes.

According to U.S. Pat. No. 4,299,775, isophorone nitrile is prepared by reacting isophorone with an aqueous solution of a cyanide in the presence of a phase transfer catalyst.

U.S. Pat. No. 5,011,968 discloses a process for preparing isophorone nitrile from isophorone and hydrogen cyanide in the presence of catalytic amounts of a quaternary ammonium hydroxide catalyst of the $NR_4^+OH^-$ type, where R is methyl, ethyl or butyl.

JP-A-61 033 157 (Chem. Abstr. 105, 42383u) describes the reaction of isophorone with HCN to form isophorone nitrile in the presence of a quaternary ammonium hydroxide, e.g. tetrabutylammonium hydroxide, or a quaternary phosphonium hydroxide as catalyst.

EP-A-502 707 (page 3, lines 12–17) discloses that when quaternary ammonium or quaternary phosphonium hydroxides are used as catalysts in the IPN synthesis from HCN and isophorone, they lead, owing to their strong basicity, to polymerization of HCN and the isophorone nitrile, which is undesirable.

EP-A-502 707 and the equivalent U.S. Pat. No. 5,179,221 describes the use of tetraalkylammonium halides or quaternary phosphonium halides with addition of a basic component as catalyst in the synthesis of IPN from isophorone and HCN.

A disadvantage common to all the abovementioned processes for preparing IPN is that the reactions are preferably carried out in the presence of water. For this reason, losses of isophorone, which is always used in excess, occur in the distillative work-up of the reaction products, since isophorone is known to form an azeotrope with water. A further drawback is the need to dispose of the contaminated water.

U.S. Pat. No. 5,183,915 discloses a process for preparing IPN from isophorone and hydrogen cyanide in the presence of quaternary ammonium cyanide or quaternary phosphonium cyanide catalysts. However, these catalysts are expensive and the IPN yields are in need of improvement.

DE-A-44 07 487 describes a process for preparing IPN by reacting isophorone with HCN in the presence of tetraalkylammonium hydrogen carbonates or tetraalkylammonium alkyl carbonates as catalyst.

As is generally known, tetraalkylammonium ions are thermally unstable in the presence of a base, e.g. a basic anion, and are decomposed to form a trialkylamine (Hofmann elimination; see, for example: R. T. Morrison and R. N. Boyd, Organic Chemistry, 6$^{th}$ Ed., 1992, bottom of page 854 to top of page 855). If the base is, for example, a hydroxide ion, the decomposition of the tetraalkylammonium ions occurs above about 125° C.

It is an object of the present invention to remedy the abovementioned disadvantages and to find an alternative process for preparing IPN from isophorone and HCN which gives the product in high space-time yields, based on the starting material and on the catalyst.

We have found that this object is achieved by a new and improved process for preparing 3-cyano-3,5,5-trimethylcyclohexanone (isophorone nitrile, IPN) by reacting isophorone with hydrogen cyanide at from 80 to 220° C. in the presence of a catalyst, wherein the reaction is carried out in the presence of the betaine 1,3-dimethylimidazolium-4-carboxylate.

The catalytically active betaine compound has the structure shown in formula I:

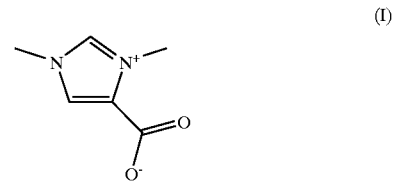

The compound I is known as a natural product under the name norzooanemonin, whose isolation and characterization has been described in Tetrahedron Lett. 38, 3883–4 (1997) and in Tetrahedron 29, 3135–(1973).

Tetrahedron 29, 3135-6 (1973) also describes the synthesis of 1,3-dimethylimidazolium-4-carboxylate (I) by reacting commercially available imidazole-4-carboxylic acid with dimethyl sulfate while controlling the pH. The betaine I initially obtained by reaction of imidazole-4-carboxylic acid with dimetyl sulfate, which is still contaminated with sodium methyl sulfate, can be used directly, without a further work-up step, as catalyst in the process of the present invention for preparing IPN from isophorone and HCN.

However, the betaine I is generally, as described in loc. cit. for the synthesis of I, first purified and then used as catalyst in the process of the present invention.

The 1,3-dimethylimidazolium-4-carboxylate (I) is preferably prepared by reacting 1-methylimidazole with dimethyl carbonate as described in the German Application No 19836477.6 of the same priority date and used as catalyst in the process of the present invention.

The process of the present invention for preparing IPN from isophorone and HCN can be carried out as follows:

It is possible, for example,
a) to place isophorone together with the catalyst of the formula I into a reaction vessel and add hydrogen cyanide in an inert solvent or in isophorone or
b) to place isophorone together with hydrogen cyanide into a reaction vessel and add the catalyst of the formula I in an inert solvent or isophorone or
c) to place isophorone into a reaction vessel and add hydrogen cyanide and the catalyst of the formula I in an inert solvent or isophorone.

The variant a) is preferred.

The process can be carried out at reaction temperatures of from 80 to 220° C., preferably from 100 to 180° C., particularly preferably from 120 to 170° C.

The reaction pressure (measured as absolute pressure) is generally from 0.05 to 2 MPa, preferably from 0.09 to 1 MPa, particularly preferably atmospheric pressure.

The catalyst of the formula I is generally used in amounts of from 0.005 to 5 mol %, preferably from 0.01 to 2 mol %, particularly preferably from 0.05 to 1 mol %, based on the hydrogen cyanide used.

In the process of the present invention, the isophorone is generally used in a molar excess based on the hydrogen cyanide. The molar ratio of the two starting materials isophorone and hydrogen cyanide IP:HCN can be 2–10:1, preferably 2–5:1, particularly preferably 2–3:1.

The isophorone which remains unreacted after the reaction can be recovered by distillation.

The catalyst used according to the present invention enables particularly short residence times of the reaction mixture in the reactor to be achieved together with good yields, selectivities and high space-time yields. Depending on the reaction conditions selected, the residence times are generally from 20 minutes to a few hours.

In addition, the oligomerization or polymerization of the two starting materials isophorone and hydrogen cyanide, which is a known secondary reaction, can be virtually completely avoided and the distillation residue to be disposed of after the distillative work-up of the reaction product is thereby minimized.

Suitable reaction vessels or reactors are, for example, stirred reactors, tube reactors, cascades of stirred vessels or mixing circuits.

The process of the present invention can be carried out batchwise or preferably continuously.

For example, the process can be carried out continuously by continuously feeding the catalyst of the formula I, if desired dissolved in an inert solvent or in isophorone, into an apparatus in which isophorone is reacted continuously with hydrogen cyanide under atmospheric pressure or under superatmospheric pressure (0.09 to 1 MPa, measured as absolute pressure).

The reaction can be carried out in the presence or absence of inert solvents.

Suitable inert solvents for the reaction are water and $C_1$-$C_{20}$-alkanols, preferably $C_1$-$C_8$-alkanols, particularly preferably $C_1$-$C_4$-alkanols, such as methanol, ethanol, n-propanol, iso-propanol, n-butanol, iso-butanol and tert-butanol, aliphatic hydrocarbons having from 5 to 30 carbon atoms, preferably from 5 to 20 carbon atoms, particularly preferably from 5 to 10 carbon atoms, e.g. n-pentane, pentane isomer mixtures, n-hexane, hexane isomer mixtures, n-heptane, heptane isomer mixtures, n-octane and octane isomer mixtures, cycloaliphatic hydrocarbons having from 5 to 20 carbon atoms, preferably from 5 to 12 carbon atoms, particularly preferably from 5 to 8 carbon atoms, e.g. cyclopentane, cyclohexane, cycloheptane and cyclooctane, amides, such as dimethylformamide, dimethylacetamide and N-methylpyrrolidone, ureas such as N,N'-dimethylethyleneurea, N,N'-dimethylpropyleneurea and N,N,N',N'-tetra-n-butylurea, or carbonates such as ethylene carbonate and propylene carbonate.

Particularly preferably, isophorone is used in a molar excess based on HCN and no external solvent is added.

To neutralize the reaction product, it is possible to use acids, for example inorganic acids such as phosphoric acid and sulfuric acid or organic acids such as sulfonic acids, e.g. methanesulfonic acid and toluenesulfonic acid, or carboxylic acids, e.g. formic acid, acetic acid, propionic acid, malonic acid, 2-ethylhexanoic acid and adipic acid.

EXAMPLES

In the following examples of the preparation of IPN, the HCN concentration in the reaction mixtures was determined by nitric acid titration using the Volhard method (addition of the sample to be analyzed to 0.1 molar $AgNO_3$ solution and back titration using 0.1 molar KSCN solution).

Example 1

Preparation of Isophorone Nitrile (IPN)

622 g (4.5 mol) of isophorone and 1.8 g (12.9 mmol) of 1,3-dimethylimidazolium-4-carboxylate were placed in a reaction vessel and a mixture of 207.3 g (1.5 mol) of isophorone and 81.0 g (3 mol) of hydrogen cyanide was added at 150° C. over a period of about 60 minutes. The mixture was subsequently stirred further for about 60 minutes at 150° C. After cooling, the HCN concentration was determined by titration. No free hydrocyanic acid could be detected (HCN conversion>99.9%). After addition of 2.0 g of 85% strength $H_3PO_4$, the reaction product was distilled at 0.1 hPa. This gave 486 g of 3-cyano-3,5,5-trimethylcyclohexanone (98.1% based on HCN used). The amount of distillation residue was only 3% by weight, based on isophorone used.

Example 2

Preparation of Isophorone Nitrile 622 g (4.5 mol) of isophorone and 3.61 g (25.8 mmol) of 1,3-dimethylimidazolium-4-carboxylate were placed in a reaction vessel and a mixture of 207.3 g (1.5 mol) of isophorone and 81.0 g (3 mol) of hydrogen cyanide was added at 120° C. over a period of about 120 minutes. The mixture was subsequently stirred further for about 120 minutes at 120° C. After cooling, the HCN concentration was determined by titration. Free hydrocyanic acid could no longer be detected (HCN conversion>99.9%). After addition of 2.0 g of 85% strength $H_3PO_4$, the reaction product was distilled at 0.1 hPa. This gave 473 g of 3-cyano-3,5,5-trimethylcyclohexanone (95.4% based on HCN used).

Example 3

Preparation of Isophorone Nitrile 622 g (4.5 mol) of isophorone and 3.61 g (25.8 mmol) of 1,3-dimethylimidazolium-4-carboxylate were placed in a reaction vessel and a mixture of 207.3 g (1.5 mol) of isophorone and 81.0 g (3 mol) of hydrogen cyanide was added at 120° C. over a period of about 60 minutes. The mixture was subsequently stirred further for about 60 minutes at 120° C. After cooling, the HCN concentration was determined by titration. Free hydrocyanic acid could no longer be detected (HCN conversion>99.9%). After addition of 2.0 g of 85% strength $H_3PO_4$, the reaction product was distilled at 0.1 hPa. This gave 484 g of 3-cyano-3,5,5-trimethylcyclohexanone (97.7% based on HCN used).

Comparative Example I for the Preparation of IPN 81 g (3 mol) of hydrogen cyanide were added dropwise to 415 g (3 mol) of isophorone and 12 g (0.077 mol) of tetraethylammonium cyanide at 108° C. over a period of 60 minutes. After an after-reaction time of 30 minutes, the HCN concentration was 0.16%, i.e. the HCN conversion was 99%. The reaction product was neutralized with 9 g of $H_3PO_4$ and distilled. This gave 15 g of isophorone and 443.6 g of 3-cyano-3,5,5-trimethylcyclohexanone. This corresponded to a yield of 89.6% based on HCN used and 93% based on isophorone reacted. The distillation residue was 28.2 g (=6.8% by weight based on isophorone used).

Comparative Example 2 a for the Preparation of IPN 622 g (4.5 mol) of isophorone and 4.47 g (30 mmol) of tetramethylammonium methyl carbonate were placed in a reaction vessel and 288.3 g of a mixture of 1.5 mol of isophorone and 3 mol of hydrogen cyanide were added at 120° C. over a period of about 60 minutes. After all the mixture had been metered in, the HCN concentration in the reaction mixture was 20 ppm, i.e. the HCN conversion was >99.9%. 3.5 g of 85% strength $H_3PO_4$ were subsequently added and the reaction product was distilled at 0.1 hPa. This gave 426.6 g of isophorone and 476.8 g of 3-cyano-3,5,5-trimethylcyclohexanone (96.2% based on HCN used).

Comparative Example 2b for the Preparation of IPN 622 g (4.5 mol) of isophorone and 4.47 g (30 mmol) of tetramethylammonium methyl carbonate were placed in a reaction vessel and 288.3 g of a mixture of 1.5 mol of isophorone and 3 mol of hydrogen cyanide were added at 140° C. over a period of about 120 minutes. Even before all the mixture had been metered in, the temperature dropped considerably and reflux occurred (unreacted HCN). After all the mixture had been metered in, stirring was continued for another 120 minutes under reflux. The HCN conversion determined by titration was only 92%. The reaction mixture was not worked up further.

We claim:

1. A process for preparing 3-cyano-3,5,5-trimethylcyclohexanone by reacting isophorone with hydrogen cyanide at from 80 to 220° C. in the presence of a catalyst, wherein the reaction is carried out in the presence of the betaine 1,3-dimethylimidazolium-4-carboxylate.

2. A process as claimed in claim 1, wherein the reaction is carried out in the presence of from 0.005 to 5 mol % of the betain, based on hydrogen cyanide.

3. A process as claimed in claim 1, wherein the reaction is carried out at from 100 to 180° C.

4. A process as claimed in claim 1, wherein the reaction is carried out at absolute pressures of from 0.09 to 1 MPa.

5. A process as claimed in claim 1, wherein the reaction is carried out at atmospheric pressure.

* * * * *